United States Patent
Mensinger et al.

(10) Patent No.: US 11,628,255 B2
(45) Date of Patent: *Apr. 18, 2023

(54) SYSTEM FOR ADMINISTERING A MEDICAMENT

(71) Applicant: Medtronic MiniMed, Inc., Northridge, CA (US)

(72) Inventors: Michael Robert Mensinger, San Diego, CA (US); Sean Saint, San Diego, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 423 days.

This patent is subject to a terminal disclaimer.

(21) Appl. No.: 16/784,061

(22) Filed: Feb. 6, 2020

(65) Prior Publication Data
US 2020/0321095 A1 Oct. 8, 2020

Related U.S. Application Data

(63) Continuation of application No. 15/025,026, filed as application No. PCT/US2014/056336 on Sep. 18, 2014, now Pat. No. 10,754,927.
(Continued)

(51) Int. Cl.
*A61M 5/20* (2006.01)
*G16H 10/60* (2018.01)
(Continued)

(52) U.S. Cl.
CPC .......... *A61M 5/20* (2013.01); *A61M 5/31568* (2013.01); *A61M 5/31571* (2013.01);
(Continued)

(58) Field of Classification Search
CPC ........ G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00; G16H 10/60; G16H 40/63; G16H 40/67; G06Q 50/22–24; A61M 5/20; A61M 5/31568; A61M 5/31571; A61M 5/31525; A61M 2205/3553; A61M 2205/50;
(Continued)

(56) References Cited

U.S. PATENT DOCUMENTS 7,591,801 B2   9/2009 Brauker et al.
7,905,833 B2   3/2011 Brister et al.
(Continued)

FOREIGN PATENT DOCUMENTS

WO    2013053695 A1   4/2013

OTHER PUBLICATIONS

Canadian Office Action issued in corresponding Canadian Application No. 2,925,458 dated Nov. 9, 2020, 4 pages.

*Primary Examiner* — Robert W Morgan
*Assistant Examiner* — Charles P Coleman
(74) *Attorney, Agent, or Firm* — Carter, DeLuca & Farrell LLP

(57) ABSTRACT

Provided is a system for delivering and recording a dose of a medicament to a patient. Also provided is a method of administering a medicament to a patient. Additionally provided is a method of tracking usage of a medicament by a patient through a pen.

11 Claims, 2 Drawing Sheets

Related U.S. Application Data

(60) Provisional application No. 61/883,163, filed on Sep. 26, 2013.

(51) Int. Cl.
    *G16H 20/10*     (2018.01)
    *G16H 40/63*     (2018.01)
    *G16H 20/17*     (2018.01)
    *G16H 40/67*     (2018.01)
    *A61M 5/315*     (2006.01)

(52) U.S. Cl.
CPC ............. G16H 10/60 (2018.01); G16H 20/10 (2018.01); G16H 40/63 (2018.01); *A61M 5/31525* (2013.01); *A61M 2205/3553* (2013.01); *A61M 2205/50* (2013.01); *A61M 2205/52* (2013.01); *A61M 2205/581* (2013.01); *A61M 2205/582* (2013.01); *A61M 2205/583* (2013.01); *A61M 2205/8206* (2013.01); *G16H 20/17* (2018.01); *G16H 40/67* (2018.01)

(58) Field of Classification Search
CPC ........ A61M 2205/52; A61M 2205/581; A61M 2205/582; A61M 2205/583; A61M 2205/8206
USPC .................................................. 705/3, 2, 20
See application file for complete search history.

(56) References Cited

U.S. PATENT DOCUMENTS

| | | |
|---|---|---|
| 7,976,492 B2 | 7/2011 | Brauker et al. |
| 8,229,535 B2 | 7/2012 | Mensinger et al. |
| 8,231,531 B2 | 7/2012 | Brister et al. |
| 8,460,231 B2 | 6/2013 | Brauker et al. |
| 8,565,848 B2 | 10/2013 | Brister et al. |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,750,955 B2 | 6/2014 | Mensinger et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| 9,020,572 B2 | 4/2015 | Mensinger et al. |
| 9,050,413 B2 | 6/2015 | Brauker et al. |
| 9,143,569 B2 | 9/2015 | Mensinger et al. |
| 9,155,843 B2 | 10/2015 | Brauker et al. |
| 9,446,194 B2 | 9/2016 | Kamath et al. |
| 9,775,543 B2 | 10/2017 | Brister et al. |
| 9,937,293 B2 | 4/2018 | Brauker et al. |
| 9,996,668 B2 | 6/2018 | Reihman et al. |
| 10,169,539 B2 | 1/2019 | Reihman et al. |
| 10,278,580 B2 | 5/2019 | Brister et al. |
| 2005/0192557 A1 | 9/2005 | Brauker et al. |
| 2006/0036144 A1 | 2/2006 | Brister et al. |
| 2007/0038044 A1 | 2/2007 | Dobbles et al. |
| 2007/0173708 A9 | 7/2007 | Dobbles et al. |
| 2008/0262469 A1 | 10/2008 | Brister et al. |
| 2009/0036771 A1 | 2/2009 | Fago et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0185075 A1 | 7/2010 | Brister et al. |
| 2010/0261987 A1 | 10/2010 | Kamath et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0270158 A1 | 11/2011 | Brauker et al. |
| 2011/0313349 A1* | 12/2011 | Krulevitch ............ A61M 5/315 604/65 |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0197479 A1* | 8/2013 | Butler ............... A61M 5/31525 604/207 |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0114158 A1 | 4/2014 | Brister et al. |
| 2014/0114161 A1 | 4/2014 | Kamath et al. |
| 2014/0257065 A1 | 9/2014 | Brister et al. |
| 2014/0288494 A1 | 9/2014 | Brister et al. |
| 2015/0351683 A1 | 12/2015 | Brauker et al. |
| 2016/0066843 A1 | 3/2016 | Mensinger et al. |
| 2016/0081632 A1 | 3/2016 | Kamath et al. |
| 2016/0101232 A1 | 4/2016 | Kamath et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0185283 A1 | 6/2017 | Bhavaraju et al. |
| 2017/0185284 A1 | 6/2017 | Bhavaraju et al. |
| 2017/0270276 A1 | 9/2017 | Saint et al. |
| 2017/0286194 A1 | 10/2017 | Morris et al. |
| 2017/0286614 A1 | 10/2017 | Morris et al. |
| 2017/0366617 A1 | 12/2017 | Mensinger et al. |
| 2017/0367627 A1 | 12/2017 | Brister et al. |
| 2018/0185587 A1 | 7/2018 | Brauker et al. |
| 2018/0303417 A1 | 10/2018 | Mensinger et al. |
| 2018/0353698 A1 | 12/2018 | Saint et al. |
| 2019/0015020 A1 | 1/2019 | Brister et al. |
| 2019/0035500 A1 | 1/2019 | Saint et al. |
| 2019/0125224 A1 | 5/2019 | Kamath et al. |
| 2019/0132801 A1 | 5/2019 | Kamath et al. |
| 2019/0173885 A1 | 6/2019 | Kamath et al. |

* cited by examiner

SYSTEM FOR ADMINISTERING A MEDICAMENT

CROSS-REFERENCE TO RELATED APPLICATIONS

This application claims the benefit of U.S. Provisional Application No. 61/883,163, filed Sep. 26, 2013, and incorporated by reference herein in its entirety.

BACKGROUND OF THE INVENTION

(1) Field of the Invention

The invention relates generally to medicament delivery devices and specifically injector pens ("pens") and the tracking, logging and communication of the doses given thereby. More specifically, the invention provides a pen that may communicate with a companion device, and may be internet enabled and able transmit a dose directly to an internet service via e.g., Wifi, cellular technology or other transmission technology.

(2) Description of the Related Art

Many different diseases and conditions require the patient to self-administer doses of medication. These doses can be administered with either a syringe, or an injector pen ("pen"). Examples of self-administered medicaments include insulin, used to treat diabetes, folistim, used to treat infertility, morphine, for pain, interferon β1a for multiple sclerosis, and Enbrel or Aransep for rheumatoid arthritis. As with the dosing of any medication, it is sometimes hard to remember if a dose has been given. For this reason pill reminders have been developed where the patient places the medication for the day in a cup labeled with that day. Once they take their medication there is no question it has been taken because the pills are no longer in the cup. No acceptable solution to this problem exists for pen based therapies.

Insulin is delivered in three general ways, through syringes, insulin pens and pumps. Insulin pens offer the benefit of simplicity over the other two methods of delivery. Syringes require more steps to deliver a dose and pumps are more complicated to use and require a constant tether to the patient. However, there is no effective automated way to track and communicate the doses given with an insulin (or other medication delivery) pen in a simple manner. The present invention solves this problem.

Additionally, other medications such as expensive fertility drugs come with complicated set of intimidating syringes and are given to people inexperienced with self-injection. The present invention provides a less intimidating solution, and also provides connected features such as dose reminders, delivery tracking, and communication back with the health care provider which can make dose amount changes remotely.

BRIEF SUMMARY OF THE INVENTION

Provided herewith is a system for delivering and recording a dose of a medicament to a patient. The system comprises a pen, the pen comprising
 a body comprising a vial of the medicament;
 a mechanism capable of dispensing the medicament;
 a first sensor capable of determining that the pen is being used;
 a second sensor capable of detecting the size of the dose being delivered;
 a processor capable of processing dose information:
 a power source that powers the processor;
 a memory capable of storing dose information; and
 a wireless transmitter capable of communicating with a separate companion device and/or directly to an internet service.

Also provided is a method of administering a medicament to a patient. The method comprises using the above-described system to administer the medicament.

Additionally provided is a method of tracking usage of a medicament by a patient through a pen, wherein the medicament is administered from the pen in a plurality of boluses over time. The method comprises recording information about the medicament administration and storing the information on a companion device, where the information comprises the quantity and time of each administered bolus of the medicament.

DETAILED DESCRIPTION OF THE INVENTION

As used herein, the singular forms "a", "an" and "the" are intended to include the plural forms as well, unless the context clearly indicates otherwise. Additionally, the use of "or" is intended to include "and/or", unless the context clearly indicates otherwise.

As used herein, a pen is a device that can be used to inject multiple boluses (doses) of a medicament, where more than one dose can be stored in the device.

As used herein, the terms "sensor" and "switch" are used interchangeably unless a sensor or switch is specifically indicated.

Provided herewith is a system for delivering and recording a dose of a medicament to a patient. The system comprises a pen, where the pen comprises a body comprising a vial of the medicament;
 a mechanism capable of dispensing the medicament;
 a first sensor capable of determining that the pen is being used;
 a second sensor capable of detecting the size of the dose being delivered;
 a processor capable of processing dose information;
 a power source that powers the processor;
 a memory capable of storing dose information; and
 a wireless transmitter capable of communicating with a separate companion device and/or directly to an internet service.

Figure 1:
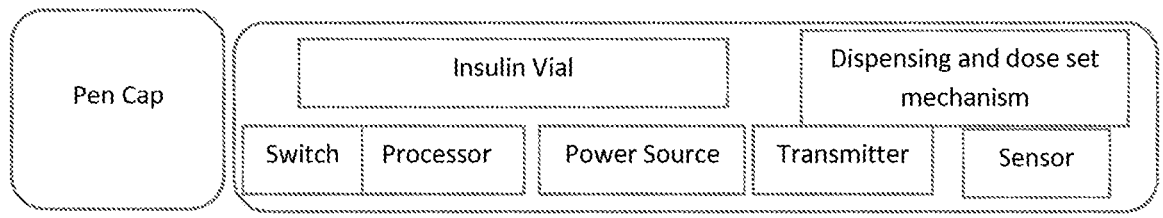
FIG. 1 shows a schematic illustration of the delivery device and its components.

FIG. 1 shows an embodiment of the pen, as used for insulin injection. The pen comprises a body which contains a drug cartridge, for example an insulin vial, which in some embodiments is replaceable. The pen also comprises a mechanism to deliver the drug (e.g., insulin). In some embodiments, the pen also comprises a mechanism for selecting the dose to be delivered, a sensor or switch ("Switch" in FIG. 1) for determining that the device is being manipulated with the intention of delivering the drug; a sensor for monitoring the dose to be delivered, a processor, a battery or other power source, a memory, and a transmitter. In some embodiments, the battery is rechargeable, in others it is non-rechargeable and non-replaceable, and in others it is non-rechargeable and replaceable by the user.

Figure 2:
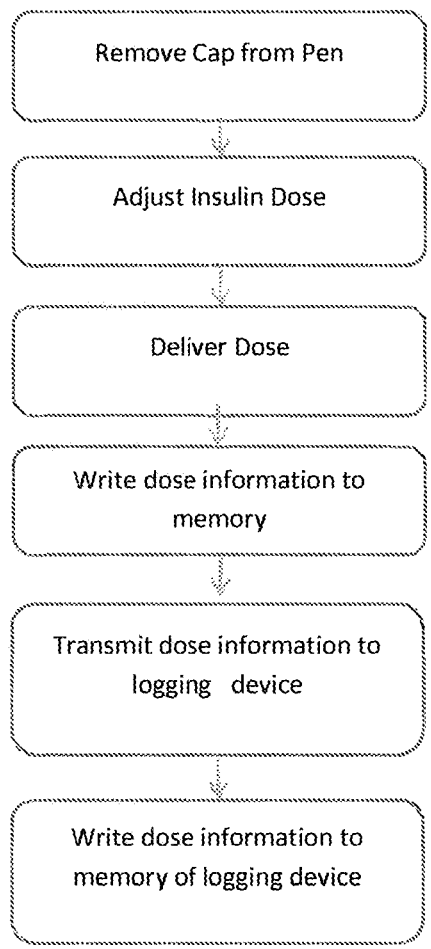
FIG. 2 shows one possible workflow for delivering a dose from the pen.
Figure 3:
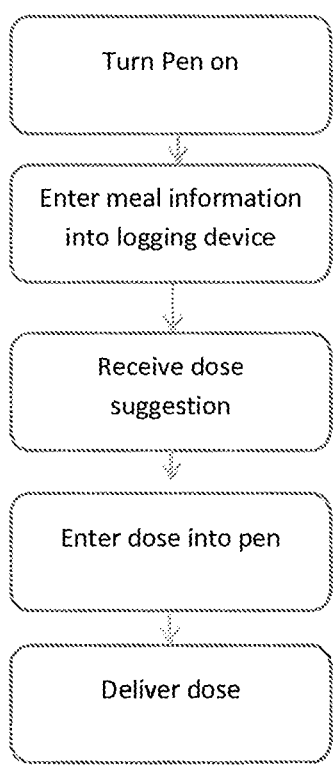
FIG. 3 shows one possible work-flow for receiving a dose recommendation from the companion device.

FIGS. 2 and 3 show examples of workflows for use of various embodiments of the pen.

While the figures exemplify the use of the system pens with insulin, the system can be utilized for administration of any medicament requiring repeated doses. Non-limiting examples include pens for delivery of infertility treatment (e.g., folistim), pain medications (e.g., morphine), multiple sclerosis treatments (e.g., interferon β1a), antiviral treatment (e.g., peginterferon α-2a) or rheumatoid arthritis treatment (e.g., Enbrel or Aransep).

The pen can communicate with one or more companion devices or directly to an internet service, through the transmitter. The invention is not limited to any particular type of transmitter, the skilled artisan could, without undue experimentation, select and utilize a transmitter useful for any particular system. In some embodiments, the transmitter is a transceiver, capable of receiving data from the companion device, or another device. In such embodiments, the system usually has software capable of processing and/or storing the incoming data.

Since the pen contains electronics and a battery or other power source, power efficiency is a primary concern for the system. In some embodiments, the processor is kept in low power mode, and activated at a programmable regular interval to advertise for communication with an external device. In some of those embodiments, this communication interval increases in frequency when the user interacts with the device.

In another embodiment, the communication with a companion device or directly with an internet service is initiated when the user begins to interact with the pen or has completed delivering a dose. For example, the processor may be turned on by a switch or sensor when the pen cap is removed or when a dose is dialed up or delivered. In the case of the pen cap being removed the switch could be a simple normally open or normally closed switch which changes position when the pen cap is removed or a proximity sensor or other electrical or mechanical device capable of detecting when the cap is removed. In the case of a sensor on the dose dial, movement of the dial (e.g., pressing on the dial or rotating the dial) could produce a sensor signal which instructs the processor to turn on. Once the device is on, in some embodiments, the user simply dials in their desired dose and delivers that dose. In other embodiments, the pen turns on when the dose is being delivered. The act of turning on the processor and dialing up the dose could be the same action, and or could utilize the same sensor. The processor then stores the size of the dose along with a time stamp for that dose. The pen can also attempt to transmit the dose and related information to the companion device or directly to the internet service.

In some embodiments, the unread records are read by the companion device from newest to oldest in order to get the most recent data fastest. In other embodiments, the records are read oldest to newest in order to simplify the syncing process.

The external device will need to read all doses since the last communication sync. This can be accomplished through any method known in the art. Nonlimiting examples include 1) the external device tracking the index of the last record read and requesting all records newer than the last read index, 2) the external device tracking the timestamp of the last read dose, and requesting all records newer than the last read timestamp, and 3) the pen marking records as transmitted or not transmitted and sending all records which have not been transmitted.

In some embodiments, the pen has limited memory capability, but the user would like a longer history of doses. In those embodiments, the companion device can store more records than the pen. In another embodiment, the companion device uploads dose information to an internet storage system. In some aspects, the dose information is synced among multiple companion devices and/or shared with health care providers, family members or anyone designated by the user. In various embodiments, the memory can store information such as dose size and time information, e.g., a length of time from when the dose was delivered until the dose was transmitted to the companion device.

The dose sensor can utilize any method of sensing rotary or linear movement known in the art. Non-limiting examples of such sensors include an electromechanical switch operatively coupled to the cap of the pen, rotary and linear encoders such as an electromechanical rotary sensor such as a Hall effect sensor or an optical encoder, or an electromechanical linear sensor such as an optical encoder or a linearly variable displacement transducers (LVDT), etc.

In some embodiments, the first sensor (capable of determining that the pen is being used) and the second sensor (capable of detecting the size of the dose being delivered) are the same sensor. Any such sensor known in the art can be utilized for these two purposes. Nonlimiting examples include suitable encoders as described above.

The delivery mechanism of the pen may be either manually powered or motorized. In either case, a force (either produced by the patient or by an electrical motor as is known in the art) pushes on the plunger of the medicament vial in order to deliver a specific amount of the medicament. In some embodiments, the mechanism can be adjusted to deliver the dose over a different period of time.

In some embodiments, software is provided, which when loaded on a companion device, allows the device to communicate with the injection device. In some of these embodiments, the software allows the patient to select the dose to be administered.

The timestamp referenced above is either the current time (i.e., user time, or UTC) or alternatively a timestamp where a count up timer is used. When the dose information is eventually transmitted to the companion device the time-since-dose is one parameter to be transmitted. In some embodiments, the time of the dose can be determined without the pen having to know the current time. This can simplify operation and setup of the pen. In another embodiment, a user time is initialized on the pen from the companion device and that time is used for dose time tracking. Using this system the companion device can know the time of the dose relative to the current time.

Once the companion device, which is for example a mobile electrical device such as a smartphone or cloud based server, receives the information it stores it in a list of doses. As used herein, the "cloud" refers to hosted internet services. The companion device can then allow the patient to browse a list of previous doses, see an estimate of current insulin active in the patient's body ("insulin on board") the calculation of which is well known in literature, or utilize a calculation system to help receive information on the size of the next dose to be delivered. For example, the patient could enter carbohydrates to be eaten and current blood sugar, and the companion device would already know insulin on board, based on previous dose history. Using these parameters a suggested insulin dose, calculated by established methods, may be determined. In one embodiment, the companion device would also allow the user to manually enter boluses into the device. This would be useful if the patient was forced to use a syringe or if the battery in the pen device died.

In some embodiments, the pen or companion device receives physiological information such as blood glucose, heart rate, blood pressure, or clinical test data from monitoring devices such as blood glucose meters or continuous glucose monitors, which can be used in the dosing calculations. This information could be manually entered, received wirelessly or through an electrical connection. In addition to being used in the dosing calculations, the most recent blood glucose information could be displayed on the companion device or pen. In instances where not only the current glucose value is known but also the rate at which the blood sugar is rising or falling, the dose calculator can use that information to subtract or add to the recommended dose respectively. Similarly, other information such as exercise, health state, altitude, temperature or other can also be used to add or subtract to the recommended dose.

At the time that the dose is to be calculated, the companion device in some embodiments verifies that it has the most up-to-date dose information by communicating with the pen. In some of those embodiments, if communication with the pen is unavailable then the automated dose calculation features would not function. This is a safety mechanism to ensure that additional insulin has not been given that has not been included in the dose calculation.

In some embodiments, the companion device transmits the calculated dose to the pen for delivery. In some embodiments, the companion device transmits the recommended dose to the pen which then provides a mechanical lock-out that prevents the user from being delivered more medicament than was calculated as a recommended dose. In another embodiment, the lockout can be enabled to prevent double dosing too close in time. In some embodiments, the lockout can be configured to allow a small amount more than the recommended dose. In further embodiments there is a method to override the dose lock out device to give a larger dose if desired, either by the user through approval on the device or on the companion device, or by health care provider, parent or other responsible party either locally or remotely through the internet. These embodiments are not narrowly limited to any particular lockout mechanisms. Nonlimiting examples of suitable lockout mechanisms are biometric, passcode or password, or a simple mental puzzle or question to confirm proper mental cognition of the user prior to allowing a potentially dangerous dose.

In other embodiments, the recommended dose can be indicated on the pen, by methods such as LCD screen, by highlighting the recommended number on the dial or by vibrating and/or sounding when the recommended dose has been reached on the dial. In automatic injection systems, the dose can be set for automatic delivery by the companion device. In some embodiments, where there is no lockout mechanism, there is an indication that the dose dialed in is more or less than the recommended or safe amount calculated. This indication may be, for example, visual through lights, colors or other, vibratory or audible signal. In some instances red indicates doses which are too large, green indicates correct dose and yellow or other indicates warning of too low of a dose, although the color may be adapted per the cultural conventions around the area or disease being treated.

In some embodiments, either the companion device or the pen is provided with a method to warn the user if a dose has been recently taken. This is a safeguard against accidentally double dosing for a meal or taking long acting insulin twice in a day. In some of these embodiments, the alarm is active if a second dose is initiated within a predefined period of time after the previous dose. In other embodiments, the alarm is configurable by the user or health care provider. When the alarm is active, any appropriate signal, e.g., audio, visual, or tactile (vibratory) can be utilized. In other embodiments either the companion device or the pen warns the user of a missed dose. A missed dose could be identified, for example, if a dose has not been given within a certain period of time after a specific time of day or after an average time of bolus. For example, with long acting insulins (for example, lantus) the injections are usually given once a day at a specific time of day. Another example is a schedule of injections of medication such as fertility treatments. The pen or companion device could average the time of the injections given on a daily basis and then give a missed dose alarm if no dose is sensed within predetermined amount of time after that average time, for example 2 hours. In other embodiments, a pattern learning algorithm learns the user's behavior and notifies of deviations. For example the algorithm notices that the user gives injections at one time during the week and at different times during weekends. It could also use location to determine different patterns, for example dosing times while traveling vs. at home.

In various embodiments, the companion device allows the dose history as well as any entered or received blood glucose data to be reviewed by a physician or the patient or other interested party such as an insurance company. This review can be exhibited on the companion devices screen and/or prepared in a report for transmission to a computer, a printer or the cloud. This transmission could occur wirelessly or through a wired interface. Wireless transmission includes upload to cloud based servers, email to a selected address or even being sent directly to a printer. e.g., through a service such as Airprint.

The present invention is also directed to a solution to the problem of the inability with present medicament injection systems to keep track of doses that have been administered. To that end, a method of tracking usage of a medicament by a patient through a pen, where the medicament is administered from the pen in a plurality of boluses over time, is provided. In this method, information is recorded about the medicament administration and the information is stored on a companion device. In these embodiments, the information comprises the quantity and time of each administered bolus of the medicament.

The pen and companion device are used by taking one or more boluses with the pen, the pen automatically storing information associated with each bolus including at a minimum the amount of the bolus and the time at which the bolus was delivered or method to determine the time and transmitting that information at some time to a companion device. In one embodiment of the invention the medicament to be infused is insulin.

The companion device to which the information can be transmitted is either a mobile electronic device, such as a smartphone or iPod touch, a tablet, a laptop, a non-mobile electronic device (for example a communication gateway such as a Qualcomm 2Net hub, computer or other) or could also be the cloud (internet based servers). The transmission could occur through any wireless protocol now known or later discovered. Examples include Bluetooth, Bluetooth low energy, Wi-Fi, zigbee or any other appropriate wireless protocol.

In addition to the dose information uploaded from the pen, in some embodiments additional dose information is entered into the companion device manually. This is to, for example, facilitate dose tracking from devices other than the pen, or when the pen is not communicating (dead battery, broken processor) or when the pen is out of range. In the case where the companion device is the cloud, a web based portal could be provided to allow entry of information.

This dose information can then be displayed to the patient, physician or other interested party. In some embodiments, this display is on the screen of the companion device or through generation and transmission of a report. The transmission of the report could be email, or direct transfer to the cloud, or direct printing or any other method of communicating the information from the device to a method of display to a person. In order to transmit the information, a contact list on the companion device may be used to select a person, address or other destination for the transmitted information to be sent to.

In various embodiments, the pen and companion device are used to generate dose recommendations for the patient. In diabetes specifically, the dose is commonly based on carbohydrates to be eaten, current blood sugar, and current insulin on board. Any or all of this information could be entered into the companion device and the device would generate a dose recommendation that the user could then take using the pen. In some embodiments, the dose recommendation is transmitted to the pen for display or injection. In other embodiments, the patient manually receives the dose recommendation from the companion device and enter it into the pen.

Because dose recommendations are based, in part, on current insulin on board, if the companion device is unaware of recent doses then the recommendation could be wrong. For that reason, in some embodiments the dose calculator does not offer a dose recommendation unless communications with the pen have recently occurred. This will ensure that the insulin on board information is up to date. Once the dose recommendation has been generated it can either be entered into the pen and dosed, or it can be viewed remotely by a third party. The dose could then be remotely approved by the third party. In some aspects, the approval allows the companion device to display the dose suggestion, and/or allow the dose suggestion to be transmitted to the pen device and/or unlock the pen device to allow injection of the dose.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

It is intended that the specification, together with the drawings, be considered exemplary only, with the scope and spirit of the invention being indicated by the claims, which follow the drawings.

REFERENCES

US Patent Application Publication 2012/0072236
US Patent Application Publication 2006/0173417
US Patent Application Publication 2011/0313349
US Patent Application Publication 2011/0275986
US Patent Application Publication 2005/0192494
US Patent Application Publication 2003/0065536
US Patent Application Publication 2005/0038674
US Patent Application Publication 2005/0049179
US Patent Application Publication 2007/0239486
US Patent Application Publication 2008/0162192
US Patent Application Publication 2008/0201169
US Patent Application Publication 2008/0235053
US Patent Application Publication 2008/0234663
U.S. Pat. No. 5,925,021
U.S. Pat. No. 6,817,986
U.S. Pat. No. 4,950,216
U.S. Pat. No. 5,279,586

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:
1. A system for recommending a dose of a medicament to a patient, comprising:
  a medicine delivery pen, comprising:
    a body structured to receive a vial of the medicament, the medicament including insulin;
    a dispensing mechanism capable of dispensing the medicament;
    a sensor capable of determining that the medicine delivery pen is being used and detecting a size of the dose being delivered;
    a processor capable of processing dose information;
    a power source that powers the processor;
    a memory capable of storing dose information; and
    a wireless transmitter capable of communicating with a separate companion device; and
  a computer program product residing in memory of the companion device, the computer program product comprising instructions, when executed by a process of the companion device, cause the system to implement steps (a)-(e):
  (a) determine a blood glucose level of the patient before an administration of insulin via the medicine delivery pen to define a determined blood glucose level;
  (b) determine a rate at which the blood glucose level of the patient is rising or falling before an administration of insulin to define a determined blood glucose trend, wherein the determined blood glucose trend is derived from a continuous blood glucose monitor that continuously monitors the blood glucose level of the patient;
  (c) based on the determined blood glucose level of step (a) and the determined blood glucose trend of step (b), automatically calculate a recommended dose of insulin to be administered to the patient;
  (d) visually present to the patient, via at least one of a display on the medicine delivery pen or a display on the companion device, the recommended dose of insulin to be administered to the patient; and

(e) administer insulin to the patient via the medicine delivery pen in an amount equal to the recommended dose of insulin visually presented to the patient in step (d).

2. The system of claim 1, wherein the computer program product further comprises instructions, which when executed by the processor of the companion device, cause the system to identify a pattern of the patient's use of the pen and generating notifications if deviations occur from the pattern.

3. The system of claim 1, wherein the companion device is a mobile electronic device.

4. The system of claim 3, wherein the mobile electronic device includes a smartphone.

5. The system of claim 1, wherein the system is configured to allow the information about the administered insulin to be entered into the companion device automatically or manually.

6. The system of claim 1, wherein the computer program product further comprises instructions, which when executed by the processor of the companion device, cause the system to, prior to administering the insulin to the patient, receive a command indicative of an approval for insulin administration by the medicine delivery pen from a remote third party device.

7. The system of claim 1, wherein the display on the medicine delivery pen is capable of displaying information recorded or calculated on the companion device and transmitted to the medicine delivery pen.

8. The system of claim 1, wherein the computer program product further comprises instructions, which when executed by the processor of the companion device, cause the companion device to generate a report of information recorded or calculated on the companion device, wherein the report can be electronically transferred, printed, emailed to a specified address, and/or uploaded to a remote server.

9. The system of claim 8, wherein the companion device has a contact list to select a contact for transmittal of the report.

10. The system of claim 1, where information about the administered insulin is viewable in real time remotely by a second companion device via sharing of data over a server.

11. The system of claim 1, wherein the computer program product further comprises instructions, which when executed by the processor of the companion device, cause the system to determine an amount of insulin on board of the patient before the administration of insulin to define an insulin on board determination, wherein calculation of step (c) includes the insulin on board determination in addition to the determined blood glucose level of step (a) and the determined blood glucose trend of step (b).

* * * * *